United States Patent [19]

Grevis et al.

[11] Patent Number: 4,895,151

[45] Date of Patent: Jan. 23, 1990

[54] APPARATUS AND METHOD FOR THERAPY ADJUSTMENT IN IMPLANTABLE

[75] Inventors: Richard Grevis, Rose Bay; Loraine Holley, Rockdale, both of Australia

[73] Assignee: Telectronics N.V., Curacao, Netherlands, Antilles

[21] Appl. No.: 75,629

[22] Filed: Jul. 20, 1987

[51] Int. Cl.$^4$ .................. A61N 1/365; A61N 1/39
[52] U.S. Cl. .................. 128/419 PG; 128/419 D
[58] Field of Search .................. 128/419 PG, 419 D

[56] References Cited

U.S. PATENT DOCUMENTS

| | | | |
|---|---|---|---|
| 4,307,725 | 12/1981 | Sowton et al. | 128/419 PG |
| 4,375,817 | 3/1983 | Engle et al. | |
| 4,384,585 | 5/1983 | Zipes | |
| 4,407,288 | 10/1983 | Langer et al. | |
| 4,473,078 | 9/1984 | Angel | 128/419 PG |
| 4,548,209 | 10/1985 | Wielders et al. | 128/419 D |
| 4,712,555 | 12/1987 | Thornander et al. | 128/419 PG |
| 4,712,556 | 12/1987 | Baker, Jr. | 128/419 PG |
| 4,750,494 | 6/1988 | King | 128/705 |
| 4,750,495 | 6/1988 | Moore et al. | 128/419 PG |
| 4,830,006 | 5/1989 | Haluska et al. | 128/419 PG |

Primary Examiner—Lee S. Cohen
Assistant Examiner—Kennedy J. Schaetzle
Attorney, Agent, or Firm—Gottlieb, Rackman & Reisman

[57] ABSTRACT

Apparatus and method for treating tachyarrhythmias wherein the presence of a patient tachyarrhythmia is detected and a first antitachyarrhythmia therapy (antitachycardia pacing) is given at a first energy level. The haemodynamic condition of the patient is measured and a length of time to therapy switchover is continually derived during the application of the first antitachyarrhythmia therapy. The length of time to switchover is a function of the haemodynamic condition of the patient. When the time following detection of the patient tachyarrhythmia exceeds the length of time to switchover, a second antitachyarrhythmia therapy (a high energy shock) at a second energy level is provided. The average cardiac cycle length may be used as an indicator of the haemodynamic condition.

20 Claims, 2 Drawing Sheets

APPARATUS AND METHOD FOR THERAPY ADJUSTMENT IN IMPLANTABLE

DESCRIPTION

This invention relates to implantable medical devices which deliver electrical energy to cardiac tissue in an attempt to terminate (revert) tachyarrhythmias and restore sinus rhythm.

As used herein, the term tachyarrhythmia refers to any fast abnormal rhythm of the heart which may be amenable to treatment by electrical discharges. This specifically includes ventricular tachycardia (VT), supraventricular tachycardia (SVT), ventricular flutter, ventricular fibrillation (VF), atrial tachycardia (AT), atrial flutter, and atrial fibrillation.

The word cardioversion refers to the discharge of electrical energy into the cardiac tissue in an attempt to terminate a tachyarrhythmia. This may be a high energy (>30J) discharge or a low energy (<1J) discharge, with a 0.1 J discharge being the minimum energy usually contemplated in cardioversion (a level much higher than that of a pacing pulse). Cardioverting shocks may or may not be synchronized to the rhythm of the heart, and defibrillation is a particular example of cardioversion.

The term cardiac cycle length refers to the measured interval in time between two successive cardiac depolarizations at the same place in the heart.

Our invention applies equally to devices which deliver energy synchronized to an R-wave and those that do not, and it applies to devices which use low energy pulses as well as devices which use high energy pulses. While the invention will usually apply to ventricular implantable cardioverters, it is equally applicable to atrial cardioverters or multiple chamber cardioverters. In general, the invention applies to any multi-mode therapy where the timing of the switchover between modes is a function of the haemodynamic condition of the patient.

By haemodynamic condition is meant the ability of the cardiac muscle and blood to successfully oxygenate the tissue of the body (in particular the brain). If sufficient oxygen is being supplied to the body, then the haemodynamic condition may be described as good (or normal or stable), whereas if there is a general lack of oxygen being supplied to the body, then the haemodynamic condition may be described as poor.

Many factors affect the haemodynamic condition of a patient and those of particular interest to our invention are electrical arrhythmias of the cardiac tissue.

PRIOR ART

Many advances are being made in the development of fully automatic implantable defibrillators and cardioverters. Recent devices contain facilities for bradycardia support and anti-tachycardia pacing, as well as cardioverting shocks from low to high energy (0.1J–80J).

While earlier implantable devices were intended to treat VF alone, current-generation implantable defibrillators are being called upon to treat VT and SVT, as well as VF. These other tachyarrhythmias are sometimes congenital in nature and, unlike VF, not always immediately fatal.

Given that the newest generation of implantable defibrillators treat a variety of cardiac conditions, it is no longer a general rule that defibrillation shocks should be administered as soon as possible. For one thing, some tachyarrhythmias may be self terminating, or haemodynamically benign, or amenable to reversion with appropriately timed trains of pacing pulses. Furthermore, in devices which are capable of delivering multiple therapies, when one kind of therapy should be terminated and the next therapy started may vary from patient to patient.

Some prior art implantable devices make no attempt to adjust the delivery of therapy on the basis of actual haemodynamic danger to the patient. The device of U.S. Pat. No. 4,407,288, for example, always delivers a large energy defibrillation shock as quickly as possible. Other prior art devices incorporate separate mechanisms for the detection of VT and VF, and select one of two available therapies dependent on whether the arrhythmia has been classified as VT or VF. Usually this differentiation mechanism is very simple, and based on heart rate alone (e.g., below 250 bpm is VT, above 250 bpm is VF). The Medtronic implantable cardioverter is an example of this kind of system, where defibrillation shocks are delivered as soon as possible for detected VF, and for VT there are four attempts at burst pacing before defibrillation shocks commence (U.S. Pat. Nos. 4,375,817 and 4,384,585); there is no continuous monitoring of haemodynamic condition or meaningful variation in the switchover time between therapies.

In reality, there does not exist a firm dividing line between pace terminable VTs and VFs. Tachyarrhythmias may vary continuously from slow, benign tachyarrhythmias, which barely need treatment; through tachyarrhythmias which are not fatal, but are unpleasant to the patient and should be treated; to very unsafe tachyarrhythmias which will result in patient death if not treated.

SUMMARY OF THE INVENTION

The prior art takes a simple approach to the timing of anti-tachyarrhythmia therapy, which can mean that sometimes cardioversion shocks are delivered sooner than necessary, and perhaps sometimes later than is prudent.

Given that cardioversion shocks may be considerably more traumatic to the patient than anti-tachyarrhythmia pacing therapy, it is desirable to delay the delivery of shocks until it is necessary to deliver them, thus avoiding shocking the patient too soon. If cardioversion shocks are delayed until needed, anti-tachyarrhythmia pacing therapy can be delivered for as long as possible, thus maximizing the chance that the tachyarrhythmia is reverted by less traumatic (and lower power) means.

The actual switchover time may be a programmable parameter, although not in the illustrative embodiment of the invention. (Pacemaker programmers are known to those skilled in the art.) For example, some physicians may not want shocks delivered until there may be some chance of brain damage, which would imply fairly extreme haemodynamic danger. Other physicians may want the first shock to be delivered just after the patient falls unconscious (to minimize patient trauma). Still others may want the first shock to be delivered as late as possible, but while the patient is still conscious, for example, if the patient must operate a machine or drive a car.

It is the object of our invention to enable the above requirements to be met, and further to provide a general mechanism for the adjustment of therapy timing or energy on the basis of haemodynamic condition. The haemodynamic state of the patient is continuously measured at least starting with the onset of the tachyarrhythmia, and that measure is used to determine the switchover time between anti-tachyarrhythmia pacing therapy and cardioversion therapy. In the illustrative embodiment of the invention, the average cardiac cycle length is used as the indicator of the haemodynamic state of the patient. The patient's haemodynamic condition is continuously measured during the anti-tachyarrhythmia pacing therapy; in this way, the switchover time can be readjusted continuously if the haemodynamic condition varies. Should a newly selected switchover time be shorter than the time during which pacing therapy has already been applied, then the switchover occurs immediately.

It is to be understood that some minimum time may be required to charge the usual capacitor which is used to deliver cardioversion shocks; this time interval is referred to as TIME-MIN herein, and may be on the order of even a few seconds. Thus although the desired switchover time is a function of haemodynamic condition, the actual switchover time in any practical pacemaker is subject to design constraints.

DETAILED DESCRIPTION OF THE ILLUSTRATIVE EMBODIMENT

Figure 1:
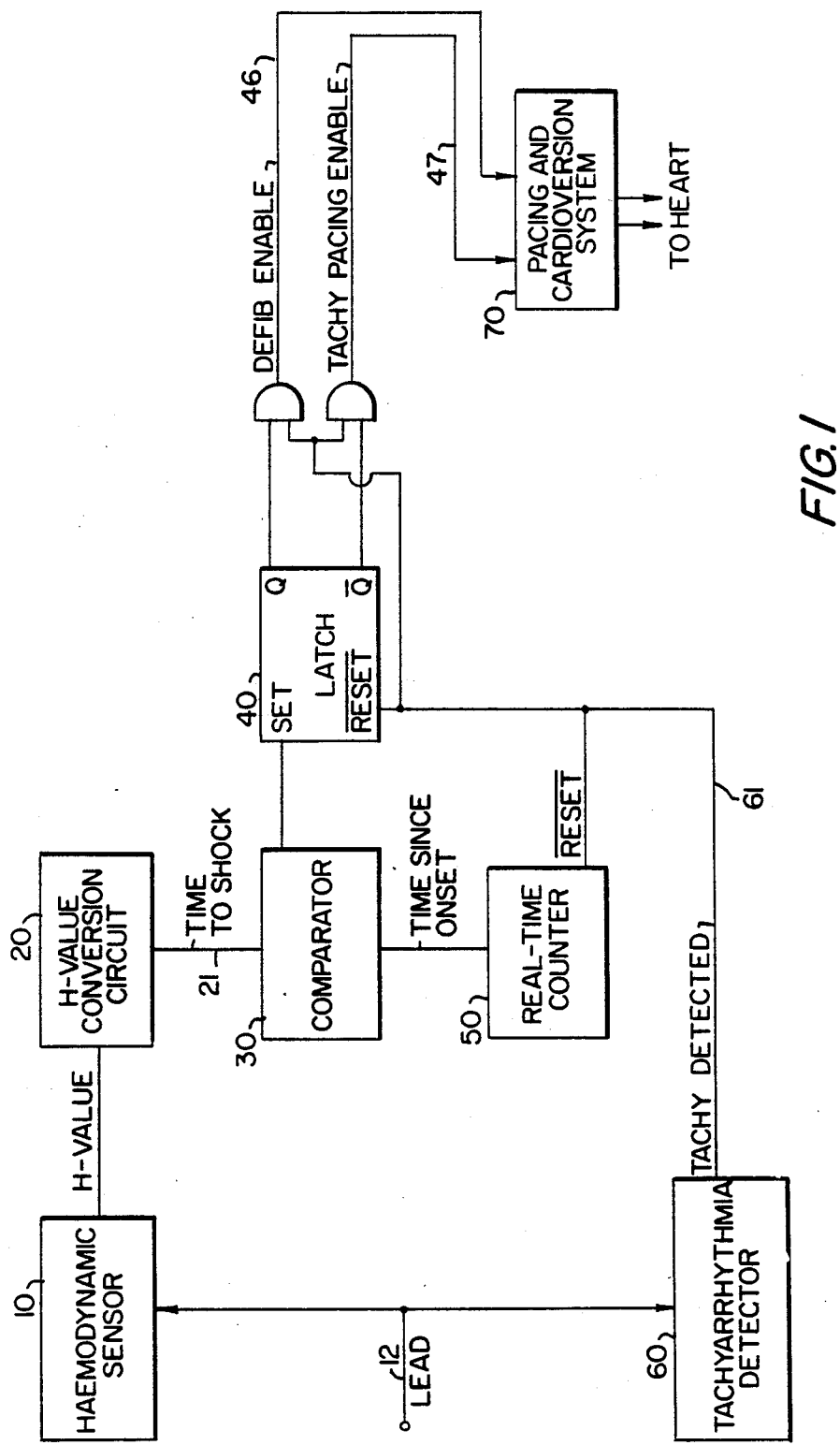
FIG. 1 is a block diagram of the illustrative embodiment of our invention, and includes the haemodynamic state sensor, conversion circuit, and therapy timer.

The illustrative embodiment of the invention shown in FIG. 1 consists of a tachyarrhythmia detection system 60, a haemodynamic sensor system 10, a conversion circuit 20 which provides a time delay, a realtime counter 50, a comparator 30, and a latch circuit 40. Sensor 10 and detector 60 have a common input in the illustrative embodiment of the invention—a lead 12 extended to the patient's heart for sensing cardiac activity.

A tachyarrhythmia is detected in a conventional manner by block 60, and the tachy detected line 61 is held high for the duration of the tachyarrhythmia episode. The apparatus and algorithm used to detect a tachyarrhythmia and confirm its continued presence may be of any type known in the art, and is not of great importance to our invention. While a tachyarrhythmia is absent, the tachy detected line 61 is held low, and real-time counter 50 and latch 40 are held reset. As a result, defib enable line 46 and tachy pacing enable line 47 are also held low.

When a tachyarrhythmia episode is detected and tachy detected line 61 goes high, real-time counter 50 starts counting, latch 40 is enabled (but not yet set), and tachy pacing enable line 47 goes high because latch 40 is initially reset. Defib enable line 46 remains low.

The haemodynamic sensor block 10 is any apparatus which can measure the haemodynamic state of the patient. While the illustrative embodiment of the invention uses the average cardiac cycle length, many other measures are also possible. These include, but are not limited to, oxygen concentration, stroke volume, blood pressure, and respiration. The actual measure used can be a nonlinear and indirect function of haemodynamic condition, and the H-value conversion circuit 20 could be made adjustable for the particular patient. More direct measures, such as stroke volume, require less physician adjustment than more indirect measures, such as heart interval (cardiac cycle length). The haemodynamic sensor block 10 yields an H-value which is related to the actual haemodynamic state of the patient H-value conversion circuit 20 can be nothing more than a ROM lookup table. The H-value indexes into the table, the table providing the required switchover time. Circuit 20 is a functional block in its most general form, but illustrative embodiments include RAM, ROM, combinatorial circuitry, or a computing element which continually calculates a time value (output) from an H-value (input). It is possible to have the conversion function programmable by the physician, so that the timing of the therapies may be tuned to a particular patient in accordance with the physicians's judgment.

The comparator 30 continually compares the required time to cardioversion shock (which itself is continually determined) with the elapsed time since tachyarrhythmia onset. When the elapsed time becomes greater than the current switchover time, the output of the comparator goes high to set latch 40. This causes defib enable line 46 to go high and tachy pacing enable line 47 to go low. It should be noted that if the required switchover time suddenly changes to a value less than the elapsed time, then the output of the comparator instantly changes state so that cardioversion shocks may begin immediately. Also, if the tachyarrhythmia episode is reverted during the pacing therapy, then the output of detector 60 goes low, both of lines 46 and 47 are disabled, and no cardioversion shocks are applied.

The two enable lines 46 and 47 sequence as described until the tachyarrhythmia has reverted, at which time they both go low, and real-time counter 50 and latch 40 are both reset.

Lines 46 and 47 are extended to pacing and cardioversion system 70. The two control lines determine the general type of therapy—pacing or shock. The particular form of either type of therapy can be any of many conventional forms, as can be the configuration of the leads extended to the patient's heart.

The illustrative embodiment of the invention produces only a tachy therapy enable signal and a defib therapy enable signal. Other embodiments of the invention may supply enable signals for a variety of other therapies, not just the ones mentioned. These signal lines may also select therapy characteristics (such as the energy of the cardioverting shocks), rather than simply enabling the therapy.

Furthermore, the comparator 30 and latch 40 which yield simple enable signals may be replaced with a functional block which takes the time to shock value (output of conversion circuit 20) and the time from onset (output of counter 50) and produces a varying signal which is a measure of patient danger. This patient danger signal (which would vary from safe to extreme danger)

would then be used to select the appropriate switchover time based on the danger measure.

Figure 2:
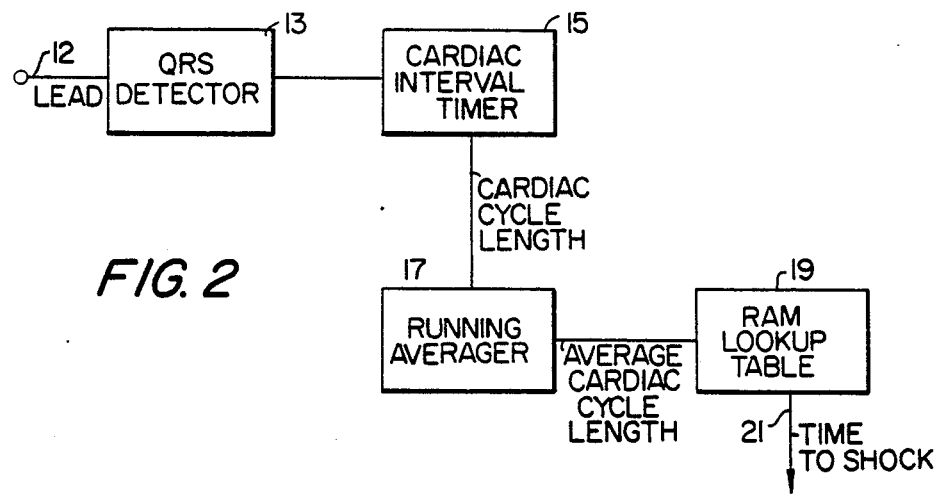
FIG. 2 depicts a particular embodiment of the haemodynamic state sensor and conversion circuit, consisting of a pacemaker-like QRS detector, an interval timer, a smoothing averager, and a RAM lookup table to convert heart intervals to a measure of haemodynamic state.

Referring now to FIG. 2, there is shown an illustrative embodiment of a haemodynamic sensor and a time conversion circuit. Cardiac depolarizations are detected by the QRS detector 13, through an electrical lead system 12, which connects to appropriate cardiac tissue. The QRS detector may be similar to any of the types found in prior art bradycardia pacemakers. However, the QRS detector must have sufficient sensitivity to detect VF rhythms as well as more organized VT and sinus rhythms. The QRS detector may or may not be equipped with a mechanism for automatic gain control (or threshold tracking) to enable reliable detection of the cardiac rhythm. VF rhythms are normally characterized by having particularly short intervals measured on the interval duration counter or cardiac interval timer 15.

The QRS detector 13 extends a digital signal to timer 15 whenever a cardiac depolarization takes place, and this resets the cardiac interval timer. The last cardiac cycle length is used by the running averager 17 to yield an average cardiac cycle length, the equivalent of an H-value. The running averager 17 is used to smooth temporary fluctuations of interval, and any embodiment which achieves this purpose is suitable. The H-value is then used to address the RAM lookup table 19, which then yields the appropriate time to the first cardioversion shock. While a RAM is a simple embodiment of the conversion circuit, any other technique which can map an H-value to a time is equally applicable. (The RAM can be programmed in any standard manner.)

Figure 3:
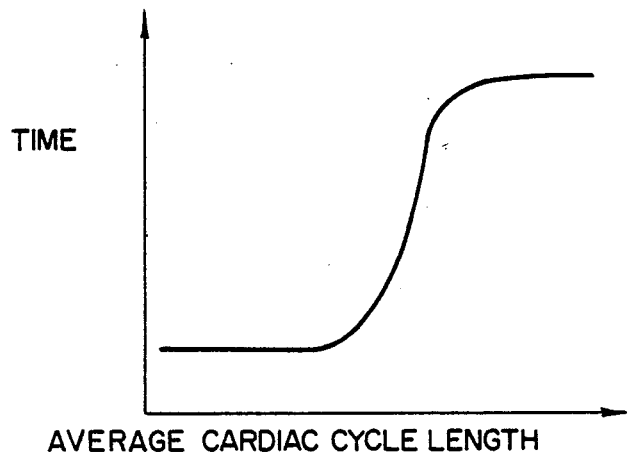
FIG. 3 shows a possible conversion function, in graphical form, between measured cardiac cycle length and the time to deliver the first cardioversion shock (switchover time) following pacing therapy.

Referring now to FIG. 3, there is shown an illustrative embodiment of the contents of the RAM table 19 shown in FIG. 2. The graph shows a general relationship between average measured cardiac cycle length and the required time to cardioversion therapy. The graph may be encoded into the RAM by storing the time values, with the address of each time value corresponding to the average measured cardiac cycle length for that time value. Given an average cardiac cycle length, that number is used as an address and the corresponding time read out. This encoding is usually referred to as a lookup table. Of course, many other encodings of the graph may be equivalently performed to achieve the same result.

Figure 4:
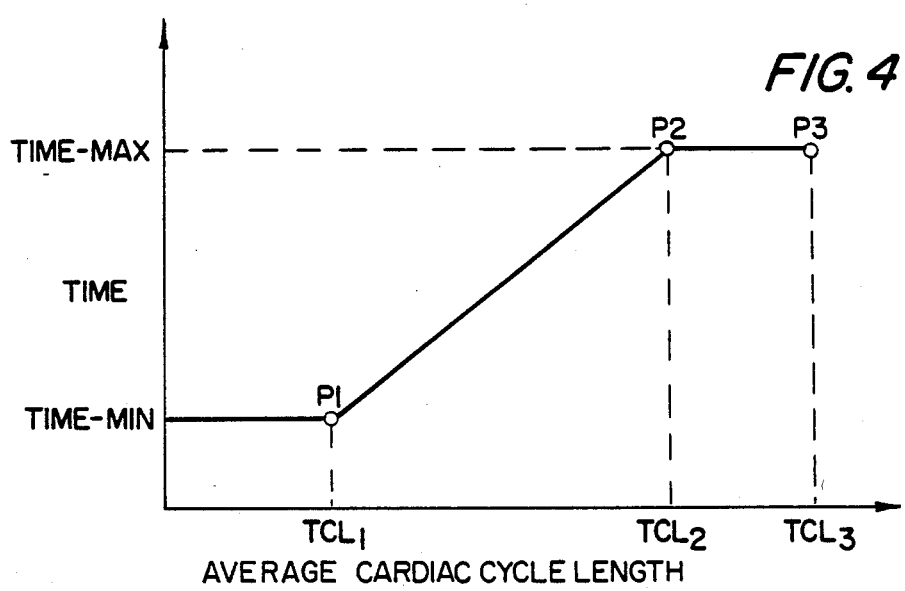
FIG. 4 shows another conversion graph between measured cardiac cycle length and the time to the first cardioversion shock, but with a smaller number of defining points on the graph.

Referring now to FIG. 4, there is shown another illustrative embodiment of the contents of the RAM lookup table 19 shown in FIG. 2. This graph shows the relationship between average measured cardiac cycle length and the required time to cardioversion therapy, but with three control points. Because three control points define the entire relationship between average cardiac cycle length and switchover time, information storage requirements are significantly reduced, and physician adjustment is significantly simplified. In the following description, it is assumed that the first cardioversion shock is delivered as soon as the defib enable line 46 goes high. It is further assumed that anti-tachyarrhythmia pacing can and does occur in the time up until the cardioversion shocks are first delivered.

Control point P1 specifies the absolute minimum time between a tachyarrhythmia onset and the assertion of the defib enable signal. For any average cardiac cycle length less than $TCL_1$, the defib enable signal will be asserted only after TIME-MIN seconds. Thus pacing therapy persists for some minimum interval.

Control point P3 specifies the maximum average cardiac cycle length for which the defib enable signal is even asserted. For any average cardiac cycle length greater than $TCL_3$, the defib enable signal is not asserted at all, and a cardioversion shock is not delivered.

Control point P2 specifies the maximum time (e.g., 15 minutes) between a tachyarrhythmia onset and the assertion of the defib enable signal, if cardioversion therapy is to be attempted. Defib enable line 46 will be asserted in TIME-MAX seconds for any average cardiac cycle length between $TCL_2$ and $TCL_3$.

For any average cardiac cycle length between $TCL_1$ and $TCL_2$, the time to assertion of the defib enable signal is proportional to the cardiac cycle length and varies between TIME-MIN and TIME-MAX as shown in the average graph.

In this illustrative embodiment of the invention, the physician may set the three control points to achieve any number of clinical timing effects. Some examples will serve to demonstrate the versatility of adjusting even these small number of control points.

If the physician wishes to have a constant or fixed delay until the first cardioversion shock, then TIME-MIN may be set equal to TIME-MAX.

If the physician wishes to emulate simple VT/VF differentiation, then $TCL_1$ may be set almost equal to $TCL_2$, but with TIME-MAX considerably longer that TIME-MIN. In this way cardioversion shocks will occur very quickly (TIME-MIN) for average cardiac cycle lengths less than the threshold, but take considerably longer (TIME-MAX) to be delivered for average cardiac cycle lengths greater than the threshold.

If the physician wishes to shock as soon as the patient has passed out, then control point P2 can be set by an electrophysiological study during which the patient is induced into a VT, and the time for the patient to fall unconscious is recorded. The time to unconsciousness and the average cardiac cycle length of the patient's VT then form control point P2. Control point P1 may be set having $TCL_1$ at 230 ms, and TIME-MIN at 7 seconds, because it has been experimentally shown that for most VT/VF rhythms less than 230 ms, a patient will be unconscious in about 6–8 seconds.

By shortening all of these times, the physician can ensure that the patient is conscious when shocked, while still allowing time for anti-tachyarrhythmia pacing if the cardiac cycle length is relatively long.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A method of treating tachyarrhythmias first comprising the steps of detecting the presence of a patient tachyarrhythmia, applying anti-tachyarrhythmia pacing therapy to the patient responsive to detection of the presence of a tachyarrhythmia, measuring the haemodynamic condition of the patient and deriving continually a derived length of time to switchover which is a function of said haemodynamic condition while said anti-tachyarrhythmia pacing therapy is continued, and immediately switching over to applying cardioversion shock therapy instead of anti-tachyarrhythmia pacing therapy after an elapsed time following the first detection of the presence of a patient tachyarrhythmia as soon as said elapsed time exceeds said derived length of time to switchover.

2. A method of treating tachyarrhythmias in accordance with claim 1 wherein the step of measuring the haemodynamic condition of the patient includes sensing average cardiac cycle length.

3. A method of treating tachyarrhythmias in accordance with claim 2 further comprising controlling said length of time to switchover to be a generally increasing function of cardiac cycle length.

4. A method of treating tachyarrhythmias in accordance with claim 3 further comprising controlling said length of time to switchover to have a maximum value.

5. A method of treating tachyarrhythmias in accordance with claim 2 further comprising said length of time to switchover to be a linear function of cardiac cycle length between a minimum time to switchover at a first cardiac cycle length and a maximum time to switchover at a second cardiac cycle length, said second cardiac cycle length being greater than said first cardiac cycle length.

6. A method of treating tachyarrhythmias in accordance with claim 1 further comprising controlling said length of time to switchover to have a maximum value.

7. A method of treating tachyarrhythmias first comprising the steps of detecting the presence of a patient tachyarrhythmia, applying to the patient a first antitachyarrhythmia therapy of a first energy level responsive to detection of the presence of a tachyarrhthmia, measuring the haemodynamic condition of the patient and continually deriving a derived length of time to switchover which is a function of said haemodynamic condition while said first antitachyarrhythmia therapy is continued, and immediately switching over to applying to the patient a second anti-tachyarrhythmia therapy at a second energy level after an elapsed time following the first detection of the presence of a patient tachyarrhythimia as soon as said elapsed time exceeds said derived length of time to switchover.

8. A method of treating tachyarrhythmias in accordance with claim 7 wherein the step of measuring the haemodynamic condition of the patient includes sensing average cardiac cycle length.

9. A method of treating tachyarrhythmias in accordance with claim 8 further comprising controlling said length of time to switchover to be a generally increasing function of cardiac cycle length.

10. A method of treating tachyarrhythmias in accordance with claim 9 further comprising controlling said length of time to switchover to have a maximum value.

11. A method of treating tachyarrhythmias in accordance with claim 8 further comprising controlling said length of time to switchover to be a linear function of cardiac cycle length between a minimum time to switchover at a first cardiac cycle length and a maximum time to switchover at a second cardiac cycle length, said second cardiac cycle length being greater than said first cardiac cycle length.

12. A method of treating tachyarrhythmias in accordance with claim 7 further comprising controlling said length of time to switchover to have a maximum value.

13. A medical device for treating tachyarrhythmias comprising means for detecting the presence of a patient tachyarrhythmia, first means responsive to said detecting means for first applying to the patient a first anti-tachyarrhythmia therapy at a first energy level, measuring and deriving means for measuring the haemodynamic condition of the patient and continually deriving during said first antitachyarrhythmia therapy a length of time to switchover during which said first antitachyarrhythmia therapy continues, said length of time being a function of said haemodynamic condition as measured by said measuring and deriving means, second means for applying to the patient a second antitachyarrhythmia therapy at a second energy level, and switchover means for causing an immediate switchover from the operation of said first means to the operation of said second means as soon as the time following operation of said detecting means exceeds said length of time until switchover.

14. A medical device for treating tachyarrhythmias in accordance with claim 13 wherein said measuring and deriving means includes sensing means, for sensing average cardiac cycle length.

15. A medical device for treating tachyarrhythmias in accordance with claim 14 wherein said switchover means includes a control means and said measuring and deriving means provides an input to said control means, said input being responsive to said sensed cardiac cycle length, so that said control means controls the length of time to switchover to be a generally increasing function of the sensed cardiac cycle length.

16. A medical device for treating tachyarrhythmias in accordance with claim 15 wherein said measuring and deriving means includes a converting means for converting the sensed average cardiac cycle length to said length of time to switchover, said converting means providing said input to said control means so that the length of time to switchover has a maximum value.

17. A medical device for treating tachyarrhythmias in accordance with claim 14 wherein said measuring and deriving means includes a converting means for converting the sensed average cardiac cycle length to said length of time to switchover, said converting means providing said input to said control means so that the length of time to switchover is a linear function of cardiac cycle length between a minimum time to switchover at a first cardiac cycle length and a maximum time to switchover at a second cardiac cycle length, said second cardiac cycle length being greater than said first cardiac cycle length.

18. A medical device for treating tachyarrhythmias in accordance with claim 13 wherein said switchover means includes a control means and said measuring and deriving means provides an input to said control means so that said control means controls the switch-over time to have a maximum value.

19. The method of claim 5 further comprising controlling said length of time to switchover to be a constant when said cardiac cycle length varies between said second cardiac cycle length and a third cardiac cycle length, said third cardiac cycle length being greater than said second cardiac cycle length.

20. A medical device for treating tachyarrhythmias in accordance with claim 17 wherein said measuring and deriving means includes a converting means for converting the sensed average cardiac cycle length to said length of time to switchover, said converting means providing said input to said control means so that said length of time to switchover is a constant when said cardiac cycle length varies between said second cardiac cycle length and a third cardiac cycle length, said third cardiac cycle length being greater than said second cardiac cycle length.

* * * * *